US008455538B2

(12) United States Patent
Tully et al.

(10) Patent No.: US 8,455,538 B2
(45) Date of Patent: Jun. 4, 2013

(54) AUGMENTED COGNITIVE TRAINING (75) Inventors: Timothy P. Tully, Cold Spring Harbor, NY (US); Filippo Cavalieri, Forest Hills, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 13/113,336

(22) Filed: May 23, 2011

(65) Prior Publication Data

US 2011/0224146 A1 Sep. 15, 2011

Related U.S. Application Data (63) Continuation of application No. 09/927,914, filed on Aug. 10, 2001, now Pat. No. 7,947,731.

(60) Provisional application No. 60/224,227, filed on Aug. 10, 2000.

(51) Int. Cl.
*A01N 43/36* (2006.01)
*A61K 31/40* (2006.01)

(52) U.S. Cl.
USPC .......................................................... 514/424

(58) Field of Classification Search
USPC .......................................................... 514/424
See application file for complete search history.

(56) References Cited

U.S. PATENT DOCUMENTS

| 4,686,225 A * | 8/1987 | King ............................. 514/283 |
| 5,059,612 A | 10/1991 | Imanishi et al. |
| 5,434,149 A | 7/1995 | Jonas et al. |
| 5,547,979 A | 8/1996 | Christensen et al. |
| 5,929,223 A | 7/1999 | Tully et al. |
| 5,965,568 A | 10/1999 | Kakihana et al. |
| 6,051,559 A | 4/2000 | Tully et al. |
| 6,270,077 B1 | 8/2001 | Cohen |
| 6,290,994 B1 | 9/2001 | Lazaro Flores et al. |

FOREIGN PATENT DOCUMENTS

| EP | 200411754 A2 | 2/1991 |
| WO | 9015534 | 12/1990 |
| WO | 9611270 | 4/1996 |
| WO | 9822137 | 5/1998 |
| WO | 0213867 A2 | 2/2002 |
| WO | 20040167227 A2 | 2/2004 |
| WO | 2004091609 A2 | 10/2004 |
| WO | 2007137181 A2 | 11/2007 |

OTHER PUBLICATIONS

Zivin, J. Neurology 50:599-603 (1998).
Meistrell, et al., Shock 8: 341-348 (1997).
Munro, et al., Am. J. Path 135: 121-132 (1989).
Barone, et al., J. Cereb. Blood Flow Metab. 19: 819-834 (1999).
Rothwell, et al., Nature Med. 2: 746-747 (1996).
Shohami et al., Cytokine and Growth Factor Reviews 10: 119-130 (1999).
Hickenbottom, et al., Neurol. Clin. 2: 379-397 (2000).
Lui, et al., Stroke 25: 1481-1488 (1994).
Nawashiro, et al., J. Cereb. Blood Flow Metab. 17: 483-490 (1997).
U.S. Department of Health Human Services "Clinical Guideline No. 16: Post-Strike Rehabilitation", AHCPR Publication No. 95/0062: (May 1995); http//www.ncbi.nlm.mih.gov/books/bv.fgi?rid+hstat6. chapter.27305 (Aug. 2009).
Dean, et al., Arch. Phys. Med. Rehabil., 81: 409-417 (2000).
Johansson, Barbro B., Stroke 31:223-230 (2000).
Lange, G. et al., Arch. Phys. Rehabil., 81: 89-94 (2000).
Liepert, J. et al., Stroke 31: 1210-1216 (2000).
Lotery, A. et al., Age and Ageing 29: 221-222 (2000).
Oddone, E. et al., Med. Care 38: 192-1104 (2000).
Greener, J. et al., Cochrane Database of Systematic Reviews 2000, Issue 4. Art No. CD000425. DOI:10.1002/14651858. CD000425.
Lincoln, N. et al., Cochrane Database of Systematic Reviews 2000, Issue 4, Art. No. CD002842. DOI: 10.1002/14651858.CD002842.
das Nair, R. et al., Cochrane Database of Systematic Reviews 2007, Issue 3, Art. No. CD002293. DOI: 10.1002/14651858.CD002293.pub2.
Weiss, B.: Differential activation and inhibition of the multiple forms of cyclic nucleotide phosphodiesterase. Adv. Cycl. Nucl. Res. 5:195-211. 1975.
Weiss, B. and Hait, W. N.: Selective cyclic nucleotide phosphodiesterase inhibitors as potential therapeutic agents. Ann. Rev. Pharmacol. Toxicol. 17:441-477, 1977.
MacDonald, E., et al.: A Novel Phosophodiesterase Type 4 Inhibitor, HT-0712, Enhances Rehabilitation-Dependent Motor Recovery and Cortical Reorganization After Focal Cortical Ischemia. Neurorehabil Neural Repair OnlineFirst, pp. 1-11, 2007.
Milner, B. et al., Neuron, 20(3) :445-468 (1998).
Bevilaqua, L. et al., Behavioural Pharmacology, 8(4) :331-338 (1997).
Silva, A.J. et al., Annu. Rev. Neurosci., 21:127-148 (1998).
Bourtchouladze, R. et al., Learning & Memory, 5:365-374 (1998).
Yin, J.C.P. et al., Cell, 81:107-115 (1995).
Josselyn, S.A. et al., Society for Neuroscience, vol. 24, Abstract 365.10 (1998).
Kogan, J.H. et al., Current Biology, 7:1-11 (1996).
Bartsch, D. et al., Cell, 83:979-992 (1995).
Pedreira, M.E. et al., Animal Learning & Behavior, 26(3) :34-43 (1998).
Bourtchuladze, R. et al., Cell, 79: 59-68 (1994).
Tully, T. et al., Cell, 79:35-47 (1994).
Guzowski, J.F. and McGaugh, J.L., Proc. Natl. Acad. Sci. USA, 94:2693-2698 (1997).

(Continued)

*Primary Examiner* — Yong Chong
(74) *Attorney, Agent, or Firm* — Don J. Pelto, Esquire; Sheppard, Mullin, Richter & Hampton LLP (57) ABSTRACT

The present invention provides methods of therapy of cognitive deficits associated with a central nervous system disorder or condition, methods of enhancing cognitive performance and methods for repeated stimulation of neuronal activity or a pattern of neuronal activity, such as that underlying a specific neuronal circuit(s). The methods comprise combining cognitive training protocols and a general administration of CREB pathway-enhancing agents.

6 Claims, 1 Drawing Sheet

OTHER PUBLICATIONS

Lamprecht, R. et al., The Joiurnal of Neuroscience, 17(21):8443-8450 (1997).
Impey, S. et al., Nature Neuroscience, 1(7):595-601 (1998).
Moore, A.N. et al., The Journal of Biological Chemistry, 271(24):14214-14220 (1996).
Murphy, D.D. and Segal, M., Proc. Natl. Acad. Sci. USA, 94:1482-1487 (1997).
Liu, F.C. and Graybiel, A.M. Neuron, 17:1133-1144 (1996).
Dubnau, J. and Tully, T., Annu. Rev. Neurosci., 21:407-444 (1998).
Ikezuz, T. et al., The EMBO Journal, 15(10):2468-2475 (1996).
Sato, N. et al., Biochemical and Biophysical Research Communications, 232:637-642 (1997).
Yamamoto-Sasaki, M. et al., Brain Research, 824:300-303 (1999).
Blendy, J.A., Brain Research, 681:8-14 (1995).
Tanaka, K. et al., NeuroReport, 10:2245-2250 (1990).
Young, D. et al., Natur Medicine 5(4): 448-453 (1999).
Pandey, S.C. et al., Alcohol. Clin. Exp. Res., 23(9):1425-1434 (1999).
Ahn, S. et al., Neuron, 23:559-568 (1999).
Pham, T.A. et al., Neuron, 22:63-72 (1999).
Glazewski, S. et al., Cerebral Cortex, 9:249-256 (1999).
Bourtchouladze, R. et al.,Proc. Natl. Acad. Sci. USA,100:18, 10518-10522 (2003).
Merck Manual; Sixteenth Edition; (1992) pp. 1454 and 1456.
Yin, J.C. P. et al., Cell, 79: 49-58 (1994).
Bach, M.E. et al., Proc. Natl. Acad. Sci. USA, 96: 5280-5285 (1999).
Escorihuela, R. M. et al., Neuroscience Letters, 247(2-3):171-174 (1998).

* cited by examiner

AUGMENTED COGNITIVE TRAINING

RELATED APPLICATIONS

This application which claims benefit under 35 U.S.C. §§120 and 119(e), is a continuation of U.S. application Ser. No. 09/927,914, filed Aug. 10, 2001 now U.S. Pat. No. 7,947, 731, which claims the benefit of U.S. Provisional Application No, 60/224,227, filed on Aug. 10, 2000. The entire teachings of these applications are incorporated herein by reference.

BACKGROUND OF THE INVENTION

An estimated 4 to 5 million Americans (about 2% of all ages and 15% of those older than age 65) have some form and degree of cognitive failure. Cognitive failure (dysfunction or loss of cognitive functions, the process by which knowledge is acquired, retained and used) commonly occurs in association with central nervous system (CNS) disorders or conditions, including age-associated memory impairment, delirium (sometimes called acute confusional state), dementia (sometimes classified as Alzheimer's or non-Alzheimer's type), Alzheimer's disease, Parkinson's disease, Huntington's disease (chorea), cerebrovascular disease (e.g., stroke, ischemia), affective disorders (e.g., depression), psychotic disorders (e.g., schizophrenia, autism (Kanner's Syndrome)), neurotic disorders (e.g., anxiety, obsessive-compulsive disorder), attention deficit disorder (ADD), subdural hematoma, normal-pressure hydrocephalus, brain tumor, head or brain trauma.

Cognitive dysfunction is typically manifested by one or more cognitive deficits, which include memory impairment (impaired ability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (i.e., planning, organizing, sequencing, abstracting).

Cognitive dysfunction causes significant impairment of social and/or occupational functioning, which can interfere with the ability of an individual to perform activities of daily living and greatly impact the autonomy and quality of life of the individual.

Cognitive training protocols are generally employed in rehabilitating individuals who have some form and degree of cognitive dysfunction. For example, cognitive training protocols are commonly employed in stroke rehabilitation and in age-related memory loss rehabilitation. Because multiple training sessions are often required before an improvement or enhancement of a specific aspect of cognitive performance (ability or function) is obtained in the individuals, cognitive training protocols are often very costly and time-consuming.

SUMMARY OF THE INVENTION

The present invention relates to a novel methodology, also referred to herein as augmented cognitive training (ACT), which can either (1) rehabilitate various forms of cognitive dysfunction more efficiently than any current method or (2) enhance normal cognitive performance (ability or function). ACT can be applied for any aspect of brain function that shows a lasting performance gain after cognitive training. Accordingly, ACT can be used in rehabilitating an animal with some form and degree of cognitive dysfunction or in enhancing (improving) normal cognitive performance in an animal. ACT can also be used to exercise appropriate neuronal circuits to fine-tune the synaptic connections of newly acquired, transplanted stem cells that differentiate into neurons.

As described herein, ACT comprises two indivisible parts: (1) a specific training protocol for each brain (cognitive) function and (2) administration of cyclic AMP response element binding protein (CREB) pathway-enhancing drugs. This combination can augment cognitive training by reducing the number of training sessions required to yield a performance gain relative to that obtained with cognitive training alone or by requiring shorter or no rest intervals between training sessions to yield a performance gain. This combination can also augment cognitive training by reducing the duration and/or number of training sessions required for the induction in a specific neuronal circuit(s) of a pattern of neuronal activity or by reducing the duration and/or number of training sessions or underlying pattern of neuronal activity required to induce CREB-dependent long-term structural/function (i.e., long-lasting) change among synaptic connections of the neuronal circuit. In this manner, ACT can improve the efficiency of existing cognitive training protocols, thereby yielding significant economic benefit.

For example, cognitive training protocols are employed in treating patients with depression (monopolor) and/or phobias to help them unlearn pathological responses associated with the depression and/or phobia(s) and learn appropriate behavior. Administration of a CREB pathway-enhancing drug in conjunction with cognitive training reduces the time and/or number of training sessions required to yield a gain in performance in these patients. As such, overall treatment is accomplished in a shorter period of time.

Similarly, cognitive training protocols are employed in treating patients with autism to help them unlearn pathological responses and to learn appropriate behavior. Administration of a CREB pathway-enhancing drug in conjunction with cognitive training reduces the time and/or number of training sessions required to yield a gain in performance in these patients.

Cognitive training protocols (e.g., physical therapy, biofeedback methods) are employed in rehabilitating stroke patients (stroke rehabilitation), particularly rehabilitating impaired or lost sensory-motor function(s). Administration of a CREB pathway-enhancing drug in conjunction with cognitive training reduces the time and/or number of training sessions required to yield a gain in performance in these patients. Faster and more efficient recovery of lost cognitive function(s) are expected as a result.

Cognitive training protocols (e.g., massed training, spaced training) are employed in learning a new language or in learning to play a new musical instrument. Administration of a CREB pathway-enhancing drug in conjunction with cognitive training reduces the time and/or number of training sessions required to yield a gain in performance. As a result, less practice (training sessions) is required to learn the new language or to learn to play the new musical instrument.

Cognitive training protocols are employed in improving learning and/or performance in individuals with learning, language or reading disabilities. Administration of a CREB pathway-enhancing drug in conjunction with cognitive training reduces the time and/or number of training sessions required to yield a gain in performance in these individuals.

Cognitive training protocols are employed to exercise neuronal circuits in individuals to fine-tune synaptic connections of newly acquired, transplanted stem cells that differentiate into neurons. Administration of a CREB pathway-enhancing drug in conjunction with cognitive training reduces the time and/or number of training sessions required for the induction in (a) specific neuronal circuit(s) of a pattern of neuronal activity in these individuals.

Cognitive training protocols are employed for repeated stimulation of neuronal activity or a pattern of neuronal activity underlying (a) specific neuronal circuit(s) in individuals. Administration of a CREB pathway-enhancing drug in conjunction with cognitive training reduces the time and/or number of training sessions and/or underlying pattern of neuronal activity required to induce CREB-dependent long-term structure/function (i.e., long-lasting) change among synaptic connections of the neuronal circuit.

As a result of the present invention, methods of enhancing a specific aspect of cognitive performance in an animal (particularly a human or other mammal or vertebrate) in need thereof are provided herein comprising (a) administering to the animal an augmenting agent which enhances CREB pathway function; and (b) training the animal under conditions sufficient to produce an improvement in performance of a cognitive task of interest by the animal. "Augmenting agents" are also referred to herein as "CREB pathway-enhancing drugs".

Methods are provided herein for treating a cognitive deficit associated with a central nervous system (CNS) disorder or condition in an animal in need of said treatment comprising (a) administering to the animal an augmenting agent which enhances CREB pathway function; and (b) training the animal under conditions sufficient to produce an improvement in performance of a particular cognitive task by the animal. CNS disorders and conditions include age-associated memory impairment, neurodegenerative diseases (e.g., Alzheimer's disease, Parkinson's disease, Huntington's disease (chorea), other senile dementia), psychiatric diseases (e.g., depression, schizophrenia, autism, attention deficit disorder), trauma dependent loss of function (e.g., cerebrovascular diseases (e.g., stroke, ischemia), brain tumor, head or brain injury), genetic defects (e.g., Rubinstein-Taybi syndrome, down syndrome) and learning disabilities.

Methods are also provided herein for therapy of a cognitive deficit associated with a CNS disorder or condition in an animal having undergone neuronal stem cell manipulation comprising (a) administering to the animal an augmenting agent which enhances CREB pathway function; and (b) training the animal under conditions sufficient to stimulate or induce neuronal activity or a pattern of neuronal activity in the animal. By "neuronal stem cell manipulation" is meant that (1) exogenous neuronal stem cells are transplanted into the brain or spinal chord of an animal or (2) endogenous neuronal stem cells are stimulated or induced to proliferate in the animal.

Methods are provided herein for repeated stimulation of neuronal activity or a pattern of neuronal activity, such as that underlying a specific neuronal circuit(s), in an animal comprising (a) administering to the animal an augmenting agent which enhances CREB pathway function; and (b) training the animal under conditions sufficient to stimulate or induce neuronal activity or a pattern of neuronal activity in the animal.

BRIEF DESCRIPTION OF THE DRAWING

The FIGURE is a schematic diagram illustrating a neuronal mechanism of brain plasticity, which forms the neurological basis for augmented cognitive training. Specific cognitive training protocols produce (experience-dependent) changes in neural activity of specific underlying neuronal circuits. This neural activity activates a biochemical process that modulates CREB-dependent gene expression. Downstream effectors of this transcription factor cascade then yield long-lasting structural and functional changes in synaptic connectivity of the circuit (i.e., long-term memory). This process of experience-dependent synaptic modification is ongoing in normal animals and usually requires multiple training sessions for most tasks. Augmentation of the CREB pathway during training will reduce the number of training sessions (or shorten the rest interval between them) required to produce the experience-dependent changes in synaptic structure and/or function.

DETAILED DESCRIPTION OF THE INVENTION

Figure 1:
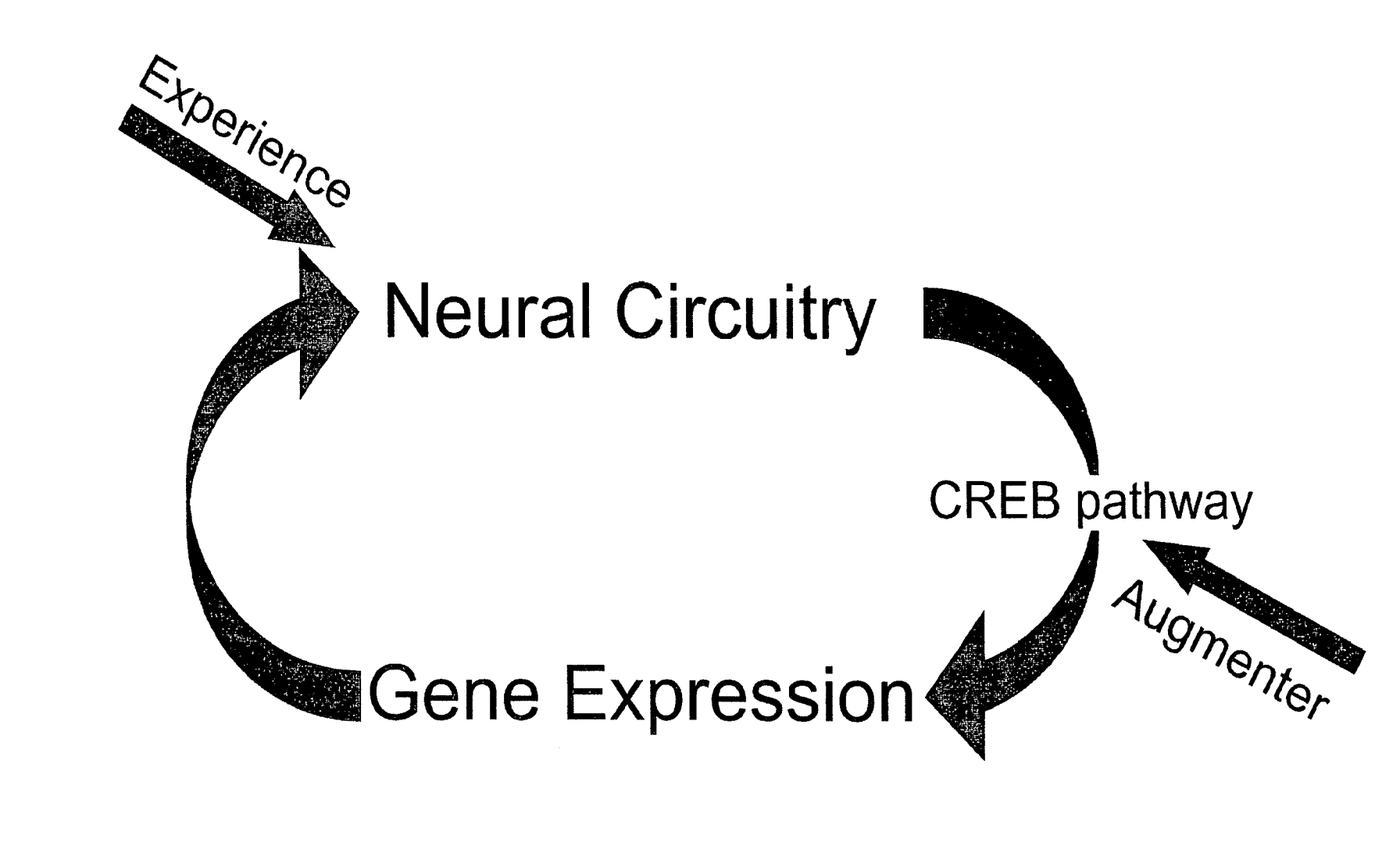

For many tasks in many species, including human, spaced training protocols (multiple training sessions with a rest interval between each) produce stronger, longer-lasting memory than massed training protocols (multiple training sessions with no rest interval in between). Behavior-genetic studies of Pavlovian olfactory learning in Drosophila have established that massed training produces a long-lasting memory that nevertheless decays away in at least four days, is not protein synthesis-dependent, is not disrupted by overexpression of a CREB-repressor transgene, and is disrupted in radish mutants (Tully, T. et al., *Cell,* 79(1):35-47 (1994); and Yin, J. C. et al., *Cell,* 79(1):49-58 (1994)). In contrast, spaced training produces a long-lasting memory that persists for at least seven days, is protein synthesis-dependent, is disrupted by overexpression of a CREB-repressor transgene and is normal in radish mutants (Tully, T. et al., *Cell,* 79(1):35-47 (1994); and Yin, J. C. et al., *Cell,* 79(1):49-58 (1994)). One day after spaced training, memory retention is composed of both the protein synthesis- and CREB-independent early memory (ARM) and the protein synthesis- and CREB-dependent long-term memory (LTM). Additional massed training is insufficient to induce LTM (Tully, T. et al., *Cell,* 79(1):35-47 (1994); and Yin, J. C. et al., *Cell,* 79(1):49-58 (1994)).

A growing body of evidence extends these results from invertebrates to mammals. For example, in *Aplysia,* molecular manipulations of CREB expression, similar to those in flies, suppress or enhance (i) LTM of a facilitatory electrophysiological response at a sensorimotor monosynapse in cell culture and (ii) the synaptic connections between sensory and motor neurons that are normally produced after spaced applications of the facilitatory stimulus (Bartsch, D. et al., *Cell,* 83(6):979-992 (1995)). In rats, injections of antisense RNA oligonucleotides into hippocampus or amygdala block LTM formation of two different tasks that are dependent on activity in these anatomical regions, respectively (Guzowski, J. F. et al., *Proc. Natl. Acad. Sci. USA,* 94(6):2693-2698 (1997); and Lamprecht, R. et al., *J. Neurosci.,* 17(21):8443-8450 (1997)). In mice, LTM formation for both implicit and explicit tasks is defective in CREB mutant mice (Bourtchuladze, R. et al., *Cell,* 79(1):59-68 (1994)).

Training of transgenic mice, carrying a CRE-dependent reporter gene (beta-galactosidase), in hippocampal-dependent contextual fear conditioning or passive avoidance tasks induces CRE-dependent reporter gene expression in areas CA1 and CA3 of the hippocampus. Training of these mice in an amygdala-dependent fear conditioning task induces CRE-dependent reporter gene expression in the amygdala, but not the hippocampus. Thus, training protocols that induce LTM formation also induce CRE-dependent gene transcription in specific anatomical areas of the mammalian brain (Impey, S. et al., *Nat. Neurosci.,* 1(7):595-601 (1998)).

With these animal models, three salient cases of LTM enhancement have been demonstrated. First, overexpression of a CREB-activator transgene abrogates the requirements for multiple, spaced training sessions and, instead, induces LTM formation after only one training session (which normally produces little or no memory retention 24 hours later (Yin, J. C. et al., *Cell,* 81(1):107-115 (1995)). Second, injection of a virally expressed CREB-activator transgene into rat amygdala also is sufficient to enhance memory after massed training for the fear-potentiated startle response, which abrogates the requirement for a rest interval in spaced training (Josselyn, S. A. et al., *Society for Neuroscience,* Vol. 24, Abstract 365.10 (1998)). Third, LTM formation in CREB-deficient mice (Bourtchuladze, R. et al., *Cell,* 79(1):59-68 (1994)) can form normally, if mutant mice are subjected to a different, spaced training protocol (Kogan, J. H. et al., *Curr. Biol.,* 7(1):1-11 (1997)).

CREB also appears involved in various forms of developmental and cellular plasticity in the vertebrate brain. For example, neuronal activity increases CREB activity in the cortex (Moore, A. N. et al., *J. Biol. Chem.,* 271(24):14214-14220 (1996)). CREB also mediates developmental plasticity in the hippocampus (Murphy, D. D. et al., *Proc. Natl. Acad. Sci. USA,* 94(4):1482-1487 (1997)), in the somatosensory cortex (Glazewski, S. et al., *Cereb. Cortex,* 9(3):249-256 (1999)), in the striatum (Liu, F. C. et al., *Neuron,* 17(6):1133-1144 (1996)), and in the visual cortex (Pham, T. A. et al., *Neuron,* 22(1):63-72 (1999)).

CREB appears to be affected in human neurodegenerative disease and brain injury. For example, CREB activation and/or expression is disrupted in Alzheimer's disease (Ikezu, T. et al., *EMBO J.,* 15(10):2468-2475 (1996); Sato, N. et al., *Biochem. Biophys. Res. Commun.,* 232(3):637-642 (1997); and Yamamoto-Sasaki, M. et al., Brain. Res., 824(2):300-303 (1999). CREB activation and/or expression is also elevated after seizures or ischemia (Blendy, J. A. et al., *Brain Res.,* 681(1-2):8-14 (1995); and Tanaka, K. et al., *Neuroreport,* 10(11):2245-2250 (1999)). "Environmental enrichment" is neuroprotective, preventing cell death by acting through CREB (Young, D. et al., *Nat. Med.,* 5(4):448-453 (1999)).

CREB functions during drug sensitivity and withdrawal. For example, CREB is affected by ethanol (Pandey, S. C. et al., *Alcohol Clin. Exp. Res.,* 23(9):1425-1434 (1999); Constantinescu, A. et al., *J. Biol. Chem.,* 274(38):26985-26991 (1999); Yang, X. et al., *Alcohol Clin. Exp. Res.,* 22(2):382-390 (1998); Yang, X. et al., *J. Neurochem.,* 70(1):224-232 (1998); and Moore, M. S. et al., *Cell,* 93(6):997-1007 (1998)), by cocaine (Carlezon, W. A., Jr. et al., *Science,* 282(5397): 2272-2275 (1998)), by morphine (Widnell, K. L. et al., *J. Pharmacol. Exp. Ther.,* 276(1):306-315 (1996)), by methamphetamine (Muratake, T. et al., *Ann N. Y. Acad. Sci.,* 844:21-26 (1998)) and by cannabinoid (Calandra, B. et al., *Eur. J. Pharmacol.,* 374(3):445-455 (1999); and Herring, A. C. et al., *Biochem. Pharmacol.,* 55(7):1013-1023 (1998)).

A signal transduction pathway that can stimulate the CREB/CRE transcriptional pathway is the cAMP regulatory system. Consistent with this, mice lacking both adenylate cyclase 1 (AC1) and AC8 enzymes fail to learn (Wong S. T. et al., *Neuron,* 23(4):787-798 (1999)). In these mice, administration of forskolin to area CA1 of the hippocampus restores learning and memory of hippocampal-dependent tasks. Furthermore, treatment of aged rats with drugs that elevate cAMP levels (such as rolipram and D1 receptor agonists) ameliorates an age-dependent loss of hippocampal-dependent memory and cellular long-term potentiation (Barad, M. et al., *Proc. Natl. Acad. Sci. USA,* 95(25):15020-15025 (1998)). These latter data suggest that a cAMP signaling is defective in learning-impaired aged rats (Bach, M. E. et al., *Proc. Natl. Acad. Sci. USA,* 96(9):5280-5285 (1999)).

The present invention relates to a novel methodology, also referred to herein as augmented cognitive training (ACT), which can (1) rehabilitate various forms of cognitive dysfunction or (2) enhance normal cognitive performance. ACT acts via a general molecular mechanism of synaptic plasticity, which apparently converts the biochemical effect of a newly acquired experience into a long-lasting structural change of the synapse. ACT can be applied for any aspect of brain function that shows a lasting performance gain after cognitive training. Accordingly, ACT can be used in rehabilitating an animal with any form of cognitive dysfunction or in enhancing or improving any aspect of normal cognitive performance in an animal.

A growing body of evidence suggests that neurons continue to proliferate in the adult brain (Arsenijevic, Y. et al., *Exp. Neurol.,* 170:48-62 (2001); Vescovi, A. L. et al., *Biomed. Pharmacother.,* 55:201-205 (2001); Cameron, H. A. and McKay, R. D., *J. Comp. Neurol.,* 435:406-417 (2001); and Geuna, S. et al., *Anat. Rec.,* 265:132-141 (2001)) and that such proliferation is in response to various experiences (Nilsson, M. et al., *J. Neurobiol.,* 39:569-578 (1999); Gould, E. et al., *Trends Cogn. Sci.,* 3:186-192 (1999); Fuchs, E. and Gould, E., *Eur. J. Neurosci.,* 12: 2211-2214 (2000); Gould, E. et al., *Biol. Psychiatry,* 48:715-720 (2000); and Gould, E. et al., *Nat. Neurosci.,* 2:260-265 (1999)). Experimental strategies now are underway to transplant neuronal stem into adult brain for various therapeutic indications (Kurimoto, Y. et al., *Neurosci. Lett.,* 306:57-60 (2001); Singh, G., *Neuropathology,* 21:110-114 (2001); and Cameron, H. A. and McKay, R. D., *Nat. Neurosci.,* 2:894-897 (1999)). Much already is known about neurogenesis in embryonic stages of development (Saitoe, M. and Tully, T., "Making connections between synaptic and behavioral plasticity in Drosophila", In *Toward a Theory of Neuroplasticity,* J. McEachern and C. Shaw, Eds. (New York: Psychology Press.), pp. 193-220 (2000)). Neuronal differentiation, neurite extension and initial synaptic target recognition all appear to occur in an activity-independent fashion. Subsequent synaptogenesis and synaptic growth, however, then requires ongoing neuronal activity to fine-tune synaptic connections in a functionally relevant manner. These findings suggest that functional (final) integration of transplanted neural stem cells require neuronal activity. Thus, ACT can be used to exercise appropriate neuronal circuits to fine-tune the synaptic connections of newly acquired, transplanted stem cells that differentiate into neurons. By "exercise appropriate neuronal circuit(s)" is meant the induction in the appropriate neuronal circuit(s) of a pattern of neuronal activity, which corresponds to that produced by a particular cognitive training protocol. The cognitive training protocol can be used to induce such neuronal activity. Alternatively, neuronal activity can be induced by direct electrical stimulation of the neuronal circuitry. "Neuronal activity" and "neural activity" are used interchangeably herein.

ACT comprises a specific training protocol for each brain function and a general administration of CREB pathway-enhancing drugs. The training protocol (cognitive training) induces neuronal activity in specific brain regions and produces improved performance of a specific brain (cognitive) function. CREB pathway-enhancing drugs, also referred to herein as augmenting agents, enhance CREB pathway function, which is required to consolidate newly acquired information into LTM. By "enhance CREB pathway function" is meant the ability to enhance or improve CREB-dependent gene expression. CREB-dependent gene expression can be enhanced or improved by increasing endogenous CREB production, for example by directly or indirectly stimulating the endogenous gene to produce increased amounts of CREB, or by increasing functional (biologically active) CREB. See, e.g., U.S. Pat. No. 5,929,223; U.S. Pat. No. 6,051,559; and International Publication No. WO9611270 (published Apr. 18, 1996), which references are incorporated herein in their entirety by reference. Administration of CREB pathway-enhancing drugs decreases the training needed to yield a performance gain relative to that yielded with training alone. In particular, ACT can enhance cognitive training by reducing the number of training sessions required to yield a performance gain relative to that yielded with cognitive training alone or by requiring shorter or no rest intervals between training sessions to yield a performance gain. In this manner, ACT can improve the efficiency of cognitive training techniques, thereby yielding significant economic benefit. By "performance gain" is meant an improvement in an aspect of cognitive performance.

The invention provides methods for enhancing a specific aspect of cognitive performance in an animal (particularly in a human or other mammal or vertebrate) in need thereof comprising (a) administering to the animal an augmenting agent which enhances CREB pathway function; and (b) training the animal under conditions sufficient to produce an improvement in performance of a particular cognitive task by the animal.

Training can comprise one or multiple training sessions and is training appropriate to produce an improvement in performance of the cognitive task of interest. For example, if an improvement in language acquisition is desired, training would focus on language acquisition. If an improvement in ability to learn to play a musical instrument is desired, training would focus on learning to play the musical instrument. If an improvement in a particular motor skill is desired, training would focus on acquisition of the particular motor skill. The specific cognitive task of interest is matched with appropriate training.

The invention also provides methods for repeated stimulation of neuronal activity or a pattern of neuronal activity, such as that underlying a specific neuronal circuit(s), in an animal comprising (a) administering to the animal an augmenting agent which enhances CREB pathway function; and (b) training the animal under conditions sufficient to stimulate or induce neuronal activity or a pattern of neuronal activity in the animal. In this case, training is training appropriate to stimulate or induce neuronal activity or a pattern of neuronal activity in the animal.

By "multiple training sessions" is meant two or more training sessions. The augmenting agent can be administered before, during or after one or more of the training sessions. In a particular embodiment, the augmenting agent is administered before and during each training session. Treatment with augmenting agent in connection with each training session is also referred to as the "augmenting treatment". By "training" is meant cognitive training.

Cognitive training protocols are known and readily available in the art. See for example, Karni, A. and Sagi, D., "Where practice makes perfect in text discrimination: evidence for primary visual cortex plasticity", *Proc. Natl. Acad. Sci. USA,* 88:4966-4970 (1991); Karni, A. and Sagi, D., "The time course of learning a visual skill", *Nature,* 365:250-252 (1993); Kramer, A. F. et al., "Task coordination and aging: explorations of executive control processes in the task switching paradigm", *Acta Psychol. (Amst.),* 101:339-378 (1999); Kramer, A. F. et al., "Training for executive control: Task coordination strategies and aging", *In Aging and Skilled Performance: Advances In Theory and Applications,* W. Rogers et al., eds. (Hillsdale, N.J.: Erlbaum) (1999); Rider, R. A. and Abdulahad, D. T., "Effects of massed versus distributed practice on gross and fine motor proficiency of educable mentally handicapped adolescents", *Percept. Mot. Skills,* 73:219-224 (1991); Willis, S. L. and Schaie, K. W., "Training the elderly on the ability factors of spatial orientation and inductive reasoning", *Psychol. Aging,* 1:239-247 (1986); Willis, S. L. and Nesselroade, C. S., "Long-term effects of fluid ability training in old-old age", *Develop. Psychol.,* 26:905-910 (1990); Wek, S. R. and Husak, W. S., "Distributed and massed practice effects on motor performance and learning of autistic children", *Percept. Mot. Skills,* 68:107-113 (1989); Verhaehen, P. et al., "Improving memory performance in the aged through mnemonic training: a meta-analytic study", *Psychol. Aging,* 7:242-251 (1992); Verhaeghen, P. and Salthouse, T. A., "Meta-analyses of age-cognition relations in adulthood: estimates of linear and nonlinear age effects and structural models", *Psychol. Bull.,* 122:231-249 (1997); Dean, C. M. et al., "Task-related circuit training improves performance of locomotor tasks in chronic stroke: a randomized, controlled pilot trial", *Arch. Phys. Med. Rehabil.,* 81:409-417 (2000); Greener, J. et al., "Speech and language therapy for aphasia following stroke", *Cochrane Database Syst. Rev.,* CD000425 (2000); Hummelsheim, H. and Eickhof, C., "Repetitive sensorimotor training for arm and hand in a patient with locked-in syndrome", *Scand. J. Rehabil. Med.,* 31:250-256 (1999); Johansson, B. B., "Brain plasticity and stroke rehabilitation. The Willis lecture", *Stroke,* 31:223-230 (2000); Ko Ko, C., "Effectiveness of rehabilitation for multiple sclerosis", *Clin. Rehabil.,* 13 (Suppl. 1):33-41 (1999); Lange, G. et al., "Organizational strategy influence on visual memory performance after stroke: cortical/subcortical and left/right hemisphere contrasts", *Arch. Phys. Med. Rehabil.,* 81:89-94 (2000); Liepert, J. et al., "Treatment-induced cortical reorganization after stroke in humans", *Stroke,* 31:1210-1216 (2000); Lotery, A. J. et al., "Correctable visual impairment in stroke rehabilitation patients", *Age Ageing,* 29:221-222 (2000); Majid, M. J. et al., "Cognitive rehabilitation for memory deficits following stroke" (Cochrane review), *Cochrane Database Syst. Rev.,* CD002293 (2000); Merzenich, M. et al., "Cortical plasticity underlying perceptual, motor, and cognitive skill development: implications for neurorehabilitation", *Cold Spring Harb. Symp. Quant. Biol.,* 61:1-8 (1996); Merzenich, M. M. et al., "Temporal processing deficits of language-learning impaired children ameliorated by training", *Science,* 271:77-81 (1996); Murphy, E., "Stroke rehabilitation", *J. R. Coll. Physicians Lond.,* 33:466-468 (1999); Nagarajan, S. S. et al., "Speech modifications algorithms used for training language learning-impaired children", *IEEE Trans. Rehabil. Eng.,* 6:257-268. (1998); Oddone, E. et al., "Quality Enhancement Research Initiative in stroke: prevention, treatment, and rehabilitation", *Med. Care* 38:I92-I104 (2000); Rice-Oxley, M. and Turner-Stokes, L., "Effectiveness of brain injury rehabilitation", *Clin. Rehabil.,* 13(Suppl 1):7-24 (1999); Tallal, P. et al., "Language learning impairments: integrating basic science, technology, and remediation", *Exp. Brain Res.,* 123:210-219 (1998); Tallal, P. et al., "Language comprehension in language-learning impaired children improved with acoustically modified speech", *Science,* 271:81-84 (1996), which references are incorporated herein in their entirety by reference.

As used herein, the term "animal" includes mammals, as well as other animals, vertebrate and invertebrate (e.g., birds, fish, reptiles, insects (e.g., Drosophila species), mollusks (e.g., Aplysia). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and primates (e.g., monkeys, chimpanzees), rodents (e.g., rats, mice, guinea pigs) and ruminents (e.g., cows, pigs, horses).

The animal can be an animal with some form and degree of cognitive dysfunction or an animal with normal cognitive performance (i.e., an animal without any form of cognitive failure (dysfunction or loss of any cognitive function)).

Cognitive dysfunction, commonly associated with brain dysfunction and central nervous system (CNS) disorders or conditions, arises due to heredity, disease, injury and/or age. CNS disorders and conditions associated with some form and degree of cognitive failure (dysfunction) include, but are not limited to the following:

1) age-associated memory impairment;
2) neurodegenerative disorders, such as delirium (acute confusional state); dementia, including Alzheimer's disease and non-Alzheimer's type dementias, such as, but not limited to, Lewy body dementia, vascular dementia, Binswanger's dementia (subcortical arteriosclerotic encephalopathy), dementias associated with Parkinson's disease, progressive supranuclear palsy, Huntington's disease (chorea), Pick's disease, normal-pressure hydrocephalus, Creutzfeldt-Jakob disease, Gerstmann-Sträussler-Scheinker disease, neurosyphilis (general paresis) or HIV infection, frontal lobe dementia syndromes, dementias associated with head trauma, including dementia pugilistica, brain trauma, subdural hematoma, brain tumor, hypothyroidism, vitamin $B_{12}$ deficiency, intracranial radiation; other neurodegenerative disorders;
3) psychiatric disorders, including affective disorders (mood disorders), such as, but not limited to, depression, including depressive pseudodementia; psychotic disorders, such as, but not limited to, schizophrenia and autism (Kanner's Syndrome); neurotic disorders, such as, but not limited to, anxiety and obsessive-compulsive disorder; attention deficit disorder;
4) trauma-dependent loss of cognitive function, such as, but not limited to that associated with (due to), cerebrovascular diseases, including stroke and ischemia, including ischemic stroke; brain trauma, including subdural hematoma and brain tumor; head injury;
5) disorders associated with some form and degree of cognitive dysfunction arising due to a genetic defect, such as, but not limited to, Rubinstein-Taybi syndrome and down syndrome;
6) learning, language or reading disabilities, particularly in children. By "learning disabilities" is meant disorders of the basic psychological processes that affect the way an individual learns. Learning disabilities can cause difficulties in listening, thinking, talking, reading, writing, spelling, arithmetic or combinations of any of the foregoing. Learning disabilities include perceptual handicaps, dyslexia and developmental aphasia.

The terms "cognitive performance" and "cognitive function" are art-recognized terms and are used herein in accordance with their art-accepted meanings. By "cognitive task" is meant a cognitive function. Cognitive functions include memory acquisition, visual discrimination, auditory discrimination, executive functioning, motor skill learning, abstract reasoning, spatial ability, speech and language skills and language acquisition. By "enhance a specific aspect of cognitive performance" is meant the ability to enhance or improve a specific cognitive or brain function, such as, for example, the acquisition of memory or the performance of a learned task. By "improvement in performance of a particular cognitive task" is meant an improvement in performance of a specific cognitive task or aspect of brain function relative to performance prior to training. For example, if after a stroke, a patient can only wiggle his or her toe, an improvement in performance (performance gain) in the patient would be the ability to walk, for example.

Accordingly, the invention also relates to methods of treating a cognitive deficit associated with a CNS disorder or condition in an animal (particularly in a human or other mammal or vertebrate) in need of said treatment comprising (a) administering to the animal an augmenting agent which enhances CREB pathway function; and (b) training the animal under conditions sufficient to produce an improvement in performance of a particular cognitive task by the animal.

In one embodiment, the invention relates to a method of treating a cognitive deficit associated with age-associated memory impairment in an animal in need of said treatment comprising (a) administering to the animal an augmenting agent which enhances CREB pathway function; and (b) training the animal under conditions sufficient to produce an improvement in performance by the animal of a cognitive task whose loss is associated with age-associated memory impairment.

In a second embodiment, the invention relates to a method of treating a cognitive deficit associated with a neurodegenerative disease (e.g., Alzheimer's disease, Parkinson's disease, Huntington's disease, other senile dementia) in an animal in need of said treatment comprising (a) administering to the animal an augmenting agent which enhances CREB pathway function; and (b) training the animal under conditions sufficient to produce an improvement in performance by the animal of a cognitive task whose deficit is associated with the neurodegenerative disease.

In a third embodiment, the invention relates to a method of treating a cognitive deficit associated with a psychiatric disease (e.g., depression, schizophrenia, autism, attention deficit disorder) in an animal in need of said treatment comprising (a) administering to the animal an augmenting agent which enhances CREB pathway function; and (b) training the animal under conditions sufficient to produce an improvement in performance by the animal of a cognitive task whose deficit is associated with the psychiatric disease.

In a fourth embodiment, the invention relates to a method of treating a cognitive deficit associated with trauma dependent loss of cognitive function (e.g., cerebrovascular diseases (e.g., stroke, ischemia), brain tumor, head or brain injury) in an animal in need of said treatment comprising (a) administering to the animal an augmenting agent which enhances CREB pathway function; and (b) training the animal under conditions sufficient to produce an improvement in performance by the animal of a cognitive task whose deficit is associated with trauma dependent loss of cognitive function.

In a fifth embodiment, the invention relates to a method of treating a cognitive deficit associated with a genetic defect (e.g., Rubinstein-Taybi syndrome, down syndrome) in an animal in need of said treatment comprising (a) administering to the animal an augmenting agent which enhances CREB pathway function; and (b) training the animal under conditions sufficient to produce an improvement in performance by the animal of a cognitive task whose deficit is associated with a genetic defect.

The invention also relates to methods of therapy of a cognitive deficit associated with a CNS disorder or condition in an animal having undergone neuronal stem cell manipulation comprising (a) administering to the animal an augmenting agent which enhances CREB pathway function; and (b) training the animal under conditions sufficient to stimulate or induce neuronal activity or a pattern of neuronal activity in the animal. By "neuronal stem cell manipulation" is meant that (1) exogenous neuronal stem cells are transplanted into the brain or spinal chord of an animal or (2) endogenous neuronal stem cells are stimulated or induced to proliferate in the animal. Methods of transplanting neuronal stem cells into the brain or spinal chord of an animal are known and readily available in the art (see, e.g., Cameron, H. A. and McKay, R. D., *Nat. Neurosci.,* 2:894-897 (1999); Kurimoto, Y. et al., *Neurosci. Lett.,* 306:57-60 (2001); and Singh, G., *Neuropathology,* 21:110-114 (2001)). Methods of stimulating or inducing proliferation of endogenous neuronal stem cells in an animal are known and readily available in the art (see, e.g., Gould, E. et al., *Trends Cogn. Sci.,* 3:186-192 (1999); Gould, E. et al., *Biol. Psychiatry,* 48:715-20 (2000); Nilsson, M. et al, *J. Neurobiol.,* 39:569-578 (1999); Fuchs, E. and Gould, E., *Eur. J. Neurosci.,* 12:2211-2214 (2000); and Gould, E. et al., *Nat. Neurosci.,* 2:260-265 (1999)). The particular methods of transplanting neuronal stem cells into the brain or spinal chord of an animal and the particular methods of stimulating or inducing proliferation of endogenous neuronal stem cells in an animal are not critical to the practice of the invention.

The invention further relates to methods of improving or enhancing learning and/or performance in an animal with a learning, language or reading disability, or combinations of any of the foregoing, comprising (a) administering to the animal an augmenting agent which enhances CREB pathway function; and (b) training the animal under conditions sufficient to produce an improvement in performance by the animal of a cognitive task associated with the disability in learning, language or reading performance.

Augmenting agents, as used herein, are compounds with pharmacological activity and include drugs, chemical compounds, ionic compounds, organic compounds, organic ligands, including cofactors, saccharides, recombinant and synthetic peptides, proteins, peptoids, nucleic acid sequences, including genes, nucleic acid products, and other molecules and compositions.

For example, augmenting agents can be cell permeant cAMP analogs (e.g, 8-bromo cAMP); activators of adenylate cyclase 1 (AC1) (e.g., forskolin); agents affecting G-protein linked receptor, such as, but not limited to adrenergic receptors and opioid receptors and their ligands (e.g., phenethylamines); modulators of intracellular calcium concentration (e.g., thapsigargin, N-methyl-D-aspartate (NMDA) receptor agonists); inhibitors of the phosphodiesterases responsible for cAMP breakdown (e.g., rolipram (which inhibits phosphodiesterase 4), iso-buto-metho-xanthine (IBMX) (which inhibits phosphodiesterases 1 and 2)); modulators of protein kinases and protein phosphatases, which mediate CREB protein activation and CREB-dependent gene expression. Augmenting agents can be exogenous CREB, CREB analogs, CREB-like molecules, biologically active CREB fragments, CREB fusion proteins, nucleic acid sequences encoding exogenous CREB, CREB analogs, CREB-like molecules, biologically active CREB fragments or CREB fusion proteins.

Augmenting agents can also be CREB function modulators, or nucleic acid sequences encoding CREB function modulators. CREB function modulators, as used herein, have the ability to modulate CREB pathway function. By "modulate" is meant the ability to change (increase or decrease) or alter CREB pathway function.

Augmenting agents can be compounds which are capable of enhancing CREB function in the CNS. Such compounds include, but are not limited to, compounds which affect membrane stability and fluidity and specific immunostimulation.

In a particular embodiment, the augmenting agent is capable of transiently enhancing CREB pathway function in the CNS.

CREB analogs, or derivatives, are defined herein as proteins having amino acid sequences analogous to endogenous CREB. Analogous amino acid sequences are defined herein to mean amino acid sequences with sufficient identity of amino acid sequence of endogenous CREB to possess the biological activity of endogenous CREB, but with one or more "silent" changes in the amino acid sequence. CREB analogs include mammalian CREM, mammalian ATF-1 and other CREB/CREM/ATF-1 subfamily members.

CREB-like molecule, as the term is used herein, refers to a protein which functionally resembles (mimics) CREB. CREB-like molecules need not have amino acid sequences analogous to endogenous CREB.

Biologically active polypeptide fragments of CREB can include only a part of the full-length amino acid sequence of CREB, yet possess biological activity. Such fragments can be produced by carboxyl or amino terminal deletions, as well as internal deletions.

Fusion proteins comprise a CREB protein as described herein, referred to as a first moiety, linked to a second moiety not occurring in the CREB protein. The second moiety can be a single amino acid, peptide or polypeptide or other organic moiety, such as a carbohydrate, a lipid or an inorganic molecule.

Nucleic acid sequences are defined herein as heteropolymers of nucleic acid molecules. The nucleic acid molecules can be double stranded or single stranded and can be a deoxyribonucleotide (DNA) molecule, such as cDNA or genomic DNA, or a ribonucleotide (RNA) molecule. As such, the nucleic acid sequence can, for example, include one or more exons, with or without, as appropriate, introns, as well as one or more suitable control sequences. In one example, the nucleic acid molecule contains a single open reading frame which encodes a desired nucleic acid product. The nucleic acid sequence is "operably linked" to a suitable promoter.

A nucleic acid sequence encoding a desired CREB protein, CREB analog (including CREM, ATF-1), CREB-like molecule, biologically active CREB fragment, CREB fusion protein or CREB function modulator can be isolated from nature, modified from native sequences or manufactured de novo, as described in, for example, Ausubel et al., *Current Protocols in Molecular Biology,* John Wiley & Sons, New York (1998); and Sambrook et al., *Molecular Cloning: A Laboratory Manual,* 2nd edition, Cold Spring Harbor University Press, New York. (1989). Nucleic acids can be isolated and fused together by methods known in the art, such as exploiting and manufacturing compatible cloning or restriction sites.

Typically, the nucleic acid sequence will be a gene which encodes the desired CREB protein, CREB analog, CREB-like molecule, CREB fusion protein or CREB function modulator. Such a gene is typically operably linked to suitable control sequences capable of effecting the expression of the CREB protein or CREB function modulator, preferably in the CNS. The term "operably linked", as used herein, is defined to mean that the gene (or the nucleic acid sequence) is linked to control sequences in a manner which allows expression of the gene (or the nucleic acid sequence). Generally, operably linked means contiguous.

Control sequences include a transcriptional promoter, an optional operator sequence to control transcription, a sequence encoding suitable messenger RNA (mRNA) ribosomal binding sites and sequences which control termination of transcription and translation. In a particular embodiment, a recombinant gene (or a nucleic acid sequence) encoding a CREB protein, CREB analog, CREB-like molecule, biologically active CREB fragment, CREB fusion protein or CREB function modulator can be placed under the regulatory control of a promoter which can be induced or repressed, thereby offering a greater degree of control with respect to the level of the product.

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. Suitable promoters are well known in the art. Exemplary promoters include the SV40 and human elongation factor (EFI). Other suitable promoters are readily available in the art (see, e.g., Ausubel et al., *Current Protocols in Molecular Biology*, John Wiley & Sons, Inc., New York (1998); Sambrook et al., *Molecular Cloning: A Laboratory Manual*, 2nd edition, Cold Spring Harbor University Press, New York (1989); and U.S. Pat. No. 5,681,735).

Augmenting agents can enhance CREB pathway function by a variety of mechanisms. For example, an augmenting agent can affect a signal transduction pathway which leads to induction of CREB-dependent gene expression. Induction of CREB-dependent gene expression can be achieved, for example, via up-regulation of positive effectors of CREB function and/or down-regulation of negative effectors of CREB function. Positive effectors of CREB function include adenylate cyclases and CREB activators. Negative effectors of CREB function include cAMP phosphodiesterase (cAMP PDE) and CREB repressors.

An augmenting agent can enhance CREB pathway function by acting biochemically upstream of or directly acting on an activator or repressor form of a CREB protein and/or on a CREB protein containing transcription complex. For example, CREB pathway function can be affected by increasing CREB protein levels transcriptionally, post-transcriptionally, or both transcriptionally and post-transcriptionally; by altering the affinity of CREB protein to other necessary components of the of the transcription complex, such as, for example, to CREB-binding protein (CBP protein); by altering the affinity of a CREB protein containing transcription complex for DNA CREB responsive elements in the promoter region; or by inducing either passive or active immunity to CREB protein isoforms. The particular mechanism by which an augmenting agent enhances CREB pathway function is not critical to the practice of the invention.

Augmenting agents can be administered directly to an animal in a variety of ways. In a preferred embodiment, augmenting agents are administered systemically. Other routes of administration are generally known in the art and include intravenous including infusion and/or bolus injection, intracerebroventricularly, intrathecal, parenteral, mucosal, implant, intraperitoneal, oral, intradermal, transdermal (e.g., in slow release polymers), intramuscular, subcutaneous, topical, epidural, etc. routes. Other suitable routes of administration can also be used, for example, to achieve absorption through epithelial or mucocutaneous linings. Particular augmenting agents can also be administered by gene therapy, wherein a DNA molecule encoding a particular therapeutic protein or peptide is administered to the animal, e.g., via a vector, which causes the particular protein or peptide to be expressed and secreted at therapeutic levels in vivo.

A vector, as the term is used herein, refers to a nucleic acid vector, e.g., a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

A nucleic acid sequence encoding a protein or peptide (e.g., CREB protein, CREB analog (including CREM, ATF-1), CREB-like molecule, biologically active CREB fragment, CREB fusion protein, CREB function modulator) can be inserted into a nucleic acid vector according to methods generally known in the art (see, e.g., Ausubel et al., Eds., *Current Protocols in Molecular Biology*, John Wiley & Sons, Inc., New York (1998); Sambrook et al., Eds., *Molecular Cloning: A Laboratory Manual*, 2nd edition, Cold Spring Harbor University Press, New York (1989)).

The mode of administration is preferably at the location of the target cells. In a particular embodiment, the mode of administration is to neurons.

Augmenting agents can be administered together with other components of biologically active agents, such as pharmaceutically acceptable surfactants (e.g., glycerides), excipients (e.g., lactose), stabilizers, preservatives, humectants, emollients, antioxidants, carriers, diluents and vehicles. If desired, certain sweetening, flavoring and/or coloring agents can also be added.

Augmenting agents can be formulated as a solution, suspension, emulsion or lyophilized powder in association with a pharmaceutically acceptable parenteral vehicle. Examples of such vehicles are water, saline, Ringer's solution, isotonic sodium chloride solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation can be sterilized by commonly used techniques. Suitable pharmaceutical carriers are described in Remington's Pharmaceutical Sciences.

The dosage of augmenting agent administered to an animal is that amount required to effect a change in CREB-dependent gene expression, particularly in neurons. The dosage administered to an animal, including frequency of administration, will vary depending upon a variety of factors, including pharmacodynamic characteristics of the particular augmenting agent, mode and route of administration; size, age, sex, health, body weight and diet of the recipient; nature and extent of symptoms being treated or nature and extent of the cognitive function(s) being enhanced or modulated, kind of concurrent treatment, frequency of treatment, and the effect desired.

Augmenting agents can be administered in single or divided doses (e.g., a series of doses separated by intervals of days, weeks or months), or in a sustained release form, depending upon factors such as nature and extent of symptoms, kind of concurrent treatment and the effect desired. Other therapeutic regimens or agents can be used in conjunction with the present invention.

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method comprising:
   (a) providing cognitive training to an animal during rehabilitation of said animal from a trauma-dependent loss of cognitive function under conditions sufficient to produce an improvement in performance by said animal of a cognitive task whose deficit is associated with said trauma-dependent loss of cognitive function;
   (b) administering to said animal in conjunction with said cognitive training an inhibitor of phosphodiesterase 1 during training;
   (c) repeating said providing and said administering of steps (a) and (b) one or more times; and
   (d) producing a long-lasting improvement in performance of said task relative to the improvement in performance of said task produced by cognitive training alone;
   wherein said trauma-dependent loss of cognitive function is associated with a cerebrovascular disease, brain trauma, or head injury.

2. A method comprising:
   (a) providing cognitive training to an animal during rehabilitation of said animal from a trauma-dependent loss of cognitive function under conditions sufficient to produce an improvement in performance by said animal of a cognitive task whose deficit is associated with said trauma-dependent loss of cognitive function;
   (b) administering to said animal in conjunction with said cognitive training an inhibitor of phosphodiesterase 1 during training;
   (c) repeating said providing and said administering of steps (a) and (b) one or more times; and
   (d) reducing the number of training sessions sufficient to produce said improvement in performance relative to the improvement in performance produced by cognitive training alone;
   wherein said trauma-dependent loss of cognitive function is associated with a cerebrovascular disease, brain trauma, or head injury.

3. The method of claim 1, wherein said cerebrovascular disease is selected from the group consisting of stroke and ischemia.

4. The method of claim 2, wherein said cerebrovascular disease is selected from the group consisting of stroke and ischemia.

5. The method of claim 1, wherein said brain trauma is selected from the group consisting of subdural hematoma and brain tumor.

6. The method of claim 2, wherein said brain trauma is selected from the group consisting of subdural hematoma and brain tumor.

* * * * *